(12) United States Patent
Vitner

(10) Patent No.: US 8,580,038 B2
(45) Date of Patent: Nov. 12, 2013

(54) PROCESS FOR THE RECOVERY OF A FERMENTATION PRODUCT

(75) Inventor: Asher Vitner, Jerusalem (IL)

(73) Assignee: Asher Vitner Ltd. (IL)

( * ) Notice: Subject to any disclaimer, the term of this patent is extended or adjusted under 35 U.S.C. 154(b) by 660 days.

(21) Appl. No.: 12/679,837

(22) PCT Filed: Sep. 18, 2008

(86) PCT No.: PCT/IL2008/001249
§ 371 (c)(1),
(2), (4) Date: Jul. 7, 2010

(87) PCT Pub. No.: WO2009/040791
PCT Pub. Date: Apr. 2, 2009

(65) Prior Publication Data
US 2010/0291646 A1 Nov. 18, 2010

(30) Foreign Application Priority Data

Sep. 24, 2007 (IL) .......................................... 186198
Sep. 4, 2008 (IL) .......................................... 193892

(51) Int. Cl.
*B01D 15/00* (2006.01)
*C07C 29/76* (2006.01)
*C12P 7/16* (2006.01)

(52) U.S. Cl.
USPC ............. 127/34; 210/638; 210/663; 210/669; 210/774; 435/160; 435/161; 568/917; 568/918

(58) Field of Classification Search
USPC ......... 210/632, 634, 638, 663, 774, 806, 669; 435/135, 155, 157, 160, 161; 159/47.1; 203/39, 41; 127/46.1, 46.3, 53, 55, 34, 127/6.24; 562/608; 568/700, 868, 916–918
See application file for complete search history.

(56) References Cited

U.S. PATENT DOCUMENTS

| | | | | |
|---|---|---|---|---|
| 3,122,486 | A | * | 2/1964 | Skarstrom et al. ............... 203/18 |
| 4,017,485 | A | * | 4/1977 | Hasegawa et al. ............ 540/221 |
| 4,273,621 | A | * | 6/1981 | Fornoff ........................... 203/19 |
| 4,450,294 | A | | 5/1984 | Feldman |
| 4,487,832 | A | | 12/1984 | Heady |
| 4,520,104 | A | * | 5/1985 | Heady et al. ................... 435/160 |
| 2007/0037259 | A1 | * | 2/2007 | Hennessey et al. ............. 435/105 |
| 2007/0161095 | A1 | * | 7/2007 | Gurin ............................. 435/134 |
| 2008/0248540 | A1 | * | 10/2008 | Yang .............................. 435/160 |

FOREIGN PATENT DOCUMENTS

| | | |
|---|---|---|
| DD | 295771 | 11/1991 |
| EP | 0112459 | 7/1984 |

OTHER PUBLICATIONS

The International Search Report corresponding to the PCT/IL2008/001249 application dated Feb. 9, 2009.

(Continued)

*Primary Examiner* — Joseph Drodge
(74) *Attorney, Agent, or Firm* — Kilpatrick Townsend & Stockton LLP

(57) ABSTRACT

The present invention provides a process for the purification and concentration of a partially water-soluble organic product from a source containing the same at concentration C0, which process comprises the steps of: (i) concentrating said product by means of a resin to form a first aqueous solution at concentration of C1; and (ii) fractionating an aqueous solution by temperature adjustment to form a second aqueous solution and a third aqueous solution with concentrations C2 and C3, respectively, wherein C2>C3 and C2>C1>C0.

3 Claims, 1 Drawing Sheet

(56) References Cited

OTHER PUBLICATIONS

Qureshi et al. "Energy-efficient recovery of butanol from model solutions and fermentation broth by adsorption" Bioprocess and Biosystems Engineering, Springer, Berlin, DE, vol. 27, No. 4, Jul. 1, 2005, pp. 215-222.

Nielsen et al. "Adsorbents for extractive bioconversion applied to the acetone-butanol fermentation" Applied Microbiology and Biotechnology, Springer Verlag, Berlin, DE, vol. 28, No. 4-5, Jun. 1, 1988, pp. 335-339.

\* cited by examiner

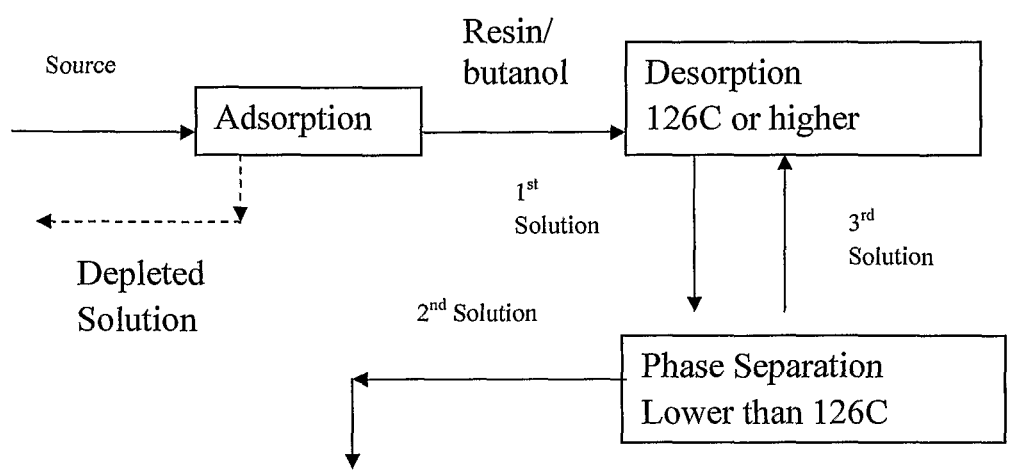

PROCESS FOR THE RECOVERY OF A FERMENTATION PRODUCT

This application is a National Stage entry under 35 U.S.C. §371 of International Application No. PCT/IL2008/001249, filed Sep. 18, 2008, and which claims the benefit of Israeli application no. 186198, filed on Sep. 24, 2007, and the Israeli application no. 193892, filed on Sep. 4, 2008, the disclosure of each of which is incorporated herein by reference in its entirety.

The present invention relates to a process for the recovery of a fermentation product. More particularly, the present invention relates to a process for the purification and concentration of a partially water-soluble organic product from a source containing the same.

Concentration and purification of dilute aqueous solutions of products is energy consuming and quite expensive. That is particularly true for products of relatively high solubility in water and ones of relatively low volatility. A specific example is provided by fermentation liquors.

Biotechnology enables genetic engineering of micro-organisms to produce an increasing number of fermentation products to be used in various applications. Biotechnological production is attractive in using renewable material as feedstock and in being conduced at about ambient temperatures. Yet, due to product inhibition, the concentration of the product in the fermentation liquor is quite low, less than 20% in most cases and less than 10% in many of them. In addition the generated fermentation liquor is contaminated with residual fermentation nutrients and fermentation co-product. Contamination is even greater when the feedstock is less refined, e.g. a hydrolyzate of lignocellulosic material. Hence, process economics depend heavily on the cost of product purification and concentration. Similar challenges are presented in some cases of products formed by extraction of products from cell material and from plant sources.

Some of the fermentation liquors are easier to handle since the product is volatile, e.g. ethanol. In other cases, the fermentation product assumes a charge at a given pH, which enables separation on ion-exchangers (amino acids) or with suitable extractants (citric acid). In still other cases, the product solubility in the broth is pH dependent, so that it can be precipitated out. A greater challenge is presented by treating solutions pf products with lower volatility that are hydrophilic in nature and do not assume charge or precipitate, e.g. alcohols, ketones and aldehydes, with more than about three carbon atoms.

Hence, there is a need for new processes for the purification and concentration of such difficult-to-separate compounds. More specifically there is a need to conduct the purification and concentration in a process that is of relatively low cost, economic in energy use and is environmentally friendly.

DESCRIPTION OF THE INVENTION

The invention provides a method for the purification and concentration of a partially water-soluble organic product from a source containing the same at concentration C0, which process comprises the steps of (i) concentrating said product by means of a resin to form a first aqueous solution with concentration of C1 and (ii) fractionating an aqueous solution by temperature adjustment to form a second aqueous solution and a third aqueous solution with concentrations C2 and C3, respectively, wherein C2>C3 and C2>C1>C0.

The product of the present invention dissolves in water but is not fully miscible with water at all temperatures, so that at given compound/water ratios and at given temperatures two phases are formed. According to a preferred embodiment, the solubility of said compound in water is temperature dependent. According to one embodiment, the solubility of the compound in water increases with temperature elevation and according to another embodiment it decreases with temperature elevation. Preferably, the product has a critical solubility temperature, Tc above which or under which it is fully miscible with water.

The product of the present invention is preferably selected from a group consisting of alcohols, ketones, aldehydes and esters with molecular weight suitable for the above-described solubility properties. Preferably, for products with solubility increasing with temperature elevation, Tc is in a range between 40 C and 200 C, more preferably between 50 C and 150 C. According to a preferred embodiment, the product is selected from a group consisting of C4, C5 and C6 alkanols, pentanol, C3, C4 and C5 aldehydes and C3, C4, and C5 ketones and more especially butanol and ethyl ethyl ketone.

Any source of the product is suitable. The product can be formed by various methods, including chemical synthesis, fermentation, enzymatic modification and extraction from various sources, such as plant material or biomass. According to a preferred embodiment, the product is a fermentation product and the source is a fermentation liquor. According to one embodiment, the fermentation product is extra cellular. According to another embodiment it is intracellular and is separated from the biomass to form the source.

Typically, the concentration of the product in the source, C0, is low, e.g. <30%, more preferably <20%, most preferably <10%. Here, and in the following, concentrations are weight concentrations and are calculated on the total weight of the solution (including product, water and other components, such as impurities). The source is an aqueous solution or an aqueous medium with some suspended solids. Typically it also comprises other components, such as residual reagents or fermentation nutrients and synthesis or fermentation coproducts. Those are generally referred to as impurities. Product purity in the source, P0, is product concentration on a water-free basis.

The process comprises a step of concentrating the product by means of a resin to form a first concentrated product. The source, as such or after some pretreatment can be contacted with a resin, whereby product is adsorbed on the resin. Various pretreatments steps could be used, depending on the composition of the source, e.g. filtration to remove insoluble components, such as biomass, changes in conditions (e.g. pH adjustment and/or heating) to denature and/or coagulate proteins, ion-exchange, etc. Upon contact with a suitable resin, the product is adsorbed on that resin.

Suitable resins are stable at the temperatures of adsorption and of desorption, T1 and T2, respectively. Preferred resins include The XRD type resins such as XRD 2, XRD 4 and others. Contact is done by known methods, e.g. in resin columns, in simulated moving-bed systems and in a chromatographic-type operation. There are no specific limitations on contact temperature, T1, as long as the resin is stable in it. Preferably T1 is close to the temperature of the source, e.g. fermentation temperature. After product adsorption, the depleted source is removed. Optionally, the product-carrying resin is washed with water to remove impurities. In a preferred embodiment, the product depleted aqueous solution is returned to the fermentation stage.

The resin is then desorbed to form a first aqueous solution with concentration of C1. Desorption is done with water or with an aqueous solution, using known methods. According to a preferred embodiment, desorption is done with a recycled aqueous stream, most preferably a recycled aqueous solution containing the product. Product concentration in the formed first solution is greater than that in the source (C1>C0). Preferably, product purity in this first aqueous solution, P1, is greater than its purity in the source (P1>P0). According to a preferred embodiment, desorption temperature, T2 is different from that of contact temperature (T1). According to a first preferred embodiment, the product solubility in water increases with temperature elevation and in that case T2>T1, more preferably, T2>Tc, most preferably T2 is less than 10 C or less than 5 C above Tc. According to another preferred embodiment, the product solubility in water decreases with temperature elevation and in that case T2<T1, more preferably, T2<Tc.

The formed first aqueous solution, as such or after some pretreatment is fractionated to form a second aqueous solution and a third aqueous solution with concentrations C2 and C3, respectively, wherein C2>C3 and C2>C1>C0. Fractionation uses adjustment of the solution temperature to T3. In cases where the solubility of the product in water increases with temperature elevation, T3<T2. In cases where the solubility of the product in water decreases with temperature elevation, T3>T2. In both cases, T3 is selected so that, at that temperature, the first solution is fractionated into at least two phases. According to a preferred embodiment, the solubility of the product in water is highly sensitive to temperature, and T3 differs from T2 by only few degrees (e.g. less than 40 C, more preferable, less than 20 C). The two phases are then separated to form two solutions, one of which forms the second solution and the other forms the third solution. Product concentration in the second solution, C2, is greater than that in the third solution, C3, and is also greater than that in the source (C0) and in the first solution, (C1). Preferably, product purity in the second solution, P2, is greater than that in the third solution, P3, and is also greater than P1 and P0. Optionally, fractionation is aided by other means, e.g. the addition of another component to the solution, pH changed, etc.

According to a preferred embodiment, the third solution is reused as such, or after adjustment, for desorption of the resin. Such adjustment may include temperature adjustment, addition or removal of components, water addition, etc.

Optionally, the second solution is further treated for product purification and/or concentration to form a product stream with concentration, C4, which is greater than C2 and/or purity, P4, which is greater than P2 and P1. Product purification may use known methods, such as adsorption, carbon treatment, ion-exchange, phase fractionation, etc. Product concentration may use various means of water removal. Thus, in case of product less volatile than water, water is distilled out of the second solution, optionally at reduced pressure. Extraction and molecular sieves could also be used.

According to a preferred embodiment, water is removed from the second solution by contacting with a stream containing a water-soluble component, which contacting induces fractionation of the second solution into two phases. According to preferred embodiments, that stream is a solid form of the water soluble component or a concentrated solution of it. Additionally, or alternatively, fractionation is induced by temperature change. Thus the temperature of the second solution is lowered in case product solubility is increased with temperature elevation, or the temperature is elevated in the opposite case. The two phases are then separated to form a product stream, where product concentration is C4, and a fifth solution, where product concentration is C5, so that C5<C4.

In cases where a water-soluble component is used to induce phase separation, most or all of it is found in the fifth solution. According to a preferred embodiment, the added water-soluble component is a salt or carbohydrate, e.g. sucrose, glucose, fructose, xylose, arabinose or mixtures of those. According to one embodiment, the fifth solution has a commercial value as such, or after some modification. According to another embodiment, it is treated for reuse in the process, e.g. by concentrating the added compound to be reused in fractionation of the second solution. According to a particularly preferred embodiment, the fifth solution is used to produce the product, e.g. as a component of the fermentation liquor. Concentration may use known methods, such as reverse osmosis, electrodialysis and evaporation.

A preferred embodiment of the present invention is demonstrated in the following for the case of recovering a fermentation-produced butanol. The main process steps are the following (see the flow diagram):

A butanol-containing fermentation liquor ("Source" in the flow diagram) is formed in a fermentation operation (not shown), where a carbohydrate is fermented to butanol. Preferably, the fermentation liquor is pretreated, e.g. centrifuged or filtered to remove biomass.

The source is then contacted with a resin ("Adsorption" in the flow diagram), whereby butanol is adsorbed on the resin, leaving a butanol-depleted aqueous stream ("Depleted Solution"). The butanol-carrying resin ("Resin/butanol") is desorbed ("Desorption") at about the critical solubility temperature of butanol, 126 C, or slightly higher temperature, by means of a recycled stream ("$3^{rd}$ Solution"). Desorption forms a solution of butanol ("$1^{st}$ solution"), which is more concentrated and more pure than the source.

This $1^{st}$ solution is cooled to a temperature of about lower than 126° C. and more preferably at 105-110 C to induce separating it into two phases ("Phase Separation")—the $2^{nd}$ Solution and the $3^{rd}$ Solution. The $3^{rd}$ Solution is a butanol solution, about 10% (depending on the Desorption temperature). It is recycled to the Desorption step, optionally after heating and some water addition.

The $2^{nd}$ Solution is a concentrated butanol solution, about 65-82% (depending on the Desorption temperature). This solution is optionally further treated for additional purification and concentration. According to a preferred embodiment (not shown in the diagram), the $3^{rd}$ solution is cooled and mixed with a concentrated solution of the same carbohydrate that is fermented in the fermentation step. Then, the phases are separated to form a concentrated butanol solution ("Product") and an aqueous solution of carbohydrate ("$5^{th}$ Solution"), which is used as part of the fermentation feedstock.

While the invention will now be described in connection with certain preferred embodiments in the following examples and with reference to the attached flow diagram, so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

In the drawings, FIG. 1 is a flow diagram of the process of the present invention.

EXAMPLES

Example No. 1

Adsorption of Butanol Upon XAD-16 at Various Temperatures Procedure

2.54 gr XAD-16, 1.619 gr Butanol and 15.9 gr water were introduced into a vial. The vial was shaken at RT for 1 hr. Sample was taken to analysis. The results are presented in Table 1.

TABLE 1

| Stage | Temperature °C. | Composition of solution Butanol Wt % | Composition in the resin Butanol/resin Wt % | Distribution D |
|---|---|---|---|---|
| Stage 1 | RT | 4.78 | 30.8 | 6.4 |

About 50% of the butanol was adsorbed in a single step at solution/XAD ratio of 6.25.

Example No. 2

Release of Butanol into an Aqueous Phase by Heating Procedure

Vial 2.54 gr XAD-16, 1.619 gr Butanol and 15.9 gr water were introduced into a vial. The vial was shaken at 122° C. for 10 minutes. A sample from the liquid was taken for analysis. The results are presented in Table 2.

The vial was cooled to RT and the vial was shaken for 30 minutes. A sample was taken for analysis. The results are presented in Table 1.

TABLE 2

| Stage | Temperature °C. | Composition of solution Butanol Wt % | Composition in the resin Butanol/resin Wt % | Distribution D |
|---|---|---|---|---|
| Stage 2 | 122 | 8.06 | 8.2 | 1.0 |

At 122° C. only about 23% of the butanol remained in the resin. Distribution coefficient at RT is 6.4 times higher than at 122° C.

Example No 3

Stage 1. 1000 gr of 5.5% was flowing into a column containing 100 gr of XAD16. The concentration of the butanol in the outlet solution was determined and is presented in Table 3.

TABLE 3

| | Weight of entering aqueous (Wt % of solution) | | | | | |
|---|---|---|---|---|---|---|
| | 100 | 200 | 400 | 600 | 700 | 800 |
| % butanol in the exiting aqueous (Wt % of solution) | 0 | 0 | 0.01 | 0.01 | 0.02 | 0.03 |

A sample from the resin XAD16 was removed and analyzed for butanol. The resin contained 35.5 wt % butanol.

200 gr of water at 125° C. were pumped into the heated column (125° C.). The exiting solution was allowed to cool to 80° C. The liquid phase formed 2 liquid phases by cooling. The lower phase contained 100 gr of aqueous solution containing about 8.9 gr butanol and about 60 gr light phase containing about 80% butanol.

60 gr light phase was pumped into a column containing 25 gr XAD 16 loaded with 35 wt % butanol. The solution and the column were heated to 125° C. The first 38.9 gr of solution was collected and allowed to cool to 80° C. The liquid phase formed 2 liquid phases by cooling. The lower phase contained 21.1 gr of aqueous solution containing about 8.9 gr butanol and about 17.1 gr light phase containing about 80% butanol.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A process for the production of butanol comprising the steps of
   (i) fermenting a carbohydrate to form a fermentation liquor comprising butanol;
   (ii) contacting said fermentation liquor, optionally after pretreatment, with a resin, whereby butanol is adsorbed to form a butanol-carrying resin;
   (iii) desorbing butanol from said butanol-carrying resin to form a first solution, wherein said desorbing comprises contacting with a third solution at a temperature higher than butanol critical solubility temperature and wherein butanol concentration in said first solution is greater than butanol concentration in the fermentation liquor; and
   (iv) cooling said first solution to a temperature below butanol critical solubility temperature, whereby two phases are formed; and separating said phases to form a second solution and a third solution, wherein butanol concentration in said second solution is greater than that in said third solution and greater than that in said first solution, wherein said desorbing of step (iii) utilizes the third solution formed in step (iv).

2. A process for the production of butanol comprising the steps of:
   (i) fermenting a carbohydrate to form a fermentation liquor comprising butanol;
   (ii) contacting said fermentation liquor, optionally after pretreatment, with a resin, whereby butanol is absorbed to form a butanol-carrying resin;
   (iii) desorbing butanol from said butanol-carrying resin to form a first solution, wherein said desorbing comprises contacting with a third solution at a temperature higher than butanol critical solubility temperature and wherein butanol concentration in said first solution is greater than butanol concentration in the fermentation liquor;
   (iv) cooling said first solution to a temperature below butanol critical solubility temperature, whereby two phases are formed; and separating said phases to form a second solution and a third solution, wherein butanol concentration in said second solution is greater than that in said third solution and greater than that in said first solution; and
   (v) mixing the second solution formed in step (iv) with a carbohydrate solution and separating into two phases, a product phase and a carbohydrate-comprising fifth solution, wherein butanol concentration in said product phase is greater than butanol concentration in said second solution.

3. A process according to claim 2, comprising using said fifth solution in said fermentation.

* * * * *